(12) United States Patent
Venkata et al.

(10) Patent No.: US 9,580,436 B2
(45) Date of Patent: *Feb. 28, 2017

(54) PROCESS OF PREPARING ALCAFTADINE (71) Applicant: Enaltec Labs Pvt. Ltd., Navi Mumbai (IN)

(72) Inventors: Sivakumar Bobba Venkata, Maharashtra (IN); Eswara Rao Kodali, Maharashtra (IN); Girish Bansilal Patel, Maharashtra (IN); Sanjay Dashrath Vaidya, Maharashtra (IN); Alok Pramod Tripathi, Maharashtra (IN)

(73) Assignee: ENALTEC LABS PRIVATE LIMITED, Navi Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/944,837

(22) Filed: Nov. 18, 2015

(65) Prior Publication Data

US 2016/0083389 A1    Mar. 24, 2016

Related U.S. Application Data (62) Division of application No. 14/391,465, filed as application No. PCT/IB2013/002585 on Nov. 19, 2013, now Pat. No. 9,255,105.

(30) Foreign Application Priority Data

Dec. 6, 2012  (IN) .......................... 3449/MUM/2012
Dec. 6, 2012  (IN) .......................... 3450/MUM/2012

(51) Int. Cl.
    *C07D 487/04*    (2006.01)
(52) U.S. Cl.
    CPC .................. *C07D 487/04* (2013.01)
(58) Field of Classification Search
    CPC .................................................. C07D 487/04
    USPC ....................................................... 540/579
    See application file for complete search history.

(56) References Cited

U.S. PATENT DOCUMENTS 9,255,105 B2 *   2/2016   Bobba Venkata ... C07D 487/04

FOREIGN PATENT DOCUMENTS

WO    WO 92/22551    * 12/1992

* cited by examiner

*Primary Examiner* — Deepak Rao
(74) *Attorney, Agent, or Firm* — Bruzga & Associates; Charles E. Bruzga; Jay S. Pattumudi (57) ABSTRACT

The present invention relates to an improved process of preparing substantially pure alcaftadine comprising reacting substantially pure compound of structural formula VIII with more than 20 moles of oxidizing reagent in an organic solvent to obtain alcaftadine:

Formula VIII

Oxidizing Reagent

Formula I

8 Claims, 2 Drawing Sheets

PROCESS OF PREPARING ALCAFTADINE

FIELD OF THE INVENTION

The field relates to an improved process of preparing substantially pure alcaftadine comprising reacting compound of structural formula VIII with more than 20 moles of oxidizing reagent in an organic solvent to obtain alcaftadine. The field also relates to a process of preparing alcaftadine compound of structural formula I by employing a substantially pure compound of structural formula VIII.

Formula VIII

BACKGROUND OF THE INVENTION

Alcaftadine is chemically 6,11-dihydro-11-(1-methyl-4-piperidinylidene)-5H-imidazo [2,1-b][3]benzazepine-3-carboxaldehyde and is known from U.S. Pat. No. 5,468,743 and is represented by a compound of structural formula I:

Formula I

Alcaftadine is a $H_1$ histamine receptor antagonist sold in USA under the proprietary name of "LASTACAFT" and is indicated for the prevention of itching associated with allergic conjunctivitis.

U.S. Pat. No. 5,468,743 describes analogous processes of preparing alcaftadine compound of structural formula I as shown below in scheme no. I, scheme no. II and scheme no. III:

Scheme I

Formula II

Formula III

Formula IV deprotection

Formula V

Formula VI

Formula VII

Formula VIII

Formula I

Formula VII

Formula VIII

Scheme II

Formula IX

Formula X

Formula XI (E)-2-butenedioate(1:2)
Formula XII

Formula I

Scheme III

Formula XIII

Formula VI

Formula VII

Formula VIII

Formula I

The processes of preparing compound of structural formula VIII according to the above mentioned references produce more than 25% of a compound of structural formula XIV:

Formula XIV

The compound of structural formula XIV is carry-forwarded into the further steps of reactions of preparing alcaftadine compound of structural formula I and therefore, there is a need in the art to develop an improved process of preparing compound of structural formula VIII, which obviates the prior-art problems.

Further, the prior art processes for preparing alcaftadine compound of structural formula I comprises treating compound of structural formula VIII with less than 20 moles of oxidizing reagent which leads to incomplete reaction and causes low yield of alcaftadine.

Accordingly, there is a need in the art to develop an improved process of preparing alcaftadine compound of structural formula I, which obviates the prior-art problems.

The inventors of the present invention have developed an improved process for the preparation of alcaftadine using substantially pure compound or purified compound of structural formula VIII, resulting in higher yield of alcaftadine. The improved process is cost effective and has fewer steps as compared to the process disclosed in the prior publications.

Further, the inventors have found that treating compound of structural formula VIII with more than 20 moles of oxidizing reagent leads to completion of reaction and results in higher yield of alcaftadine.

SUMMARY OF THE INVENTION

A first aspect of the present invention is to provide a substantially pure compound of structural formula VIII:

Formula VIII

According to another aspect, the present invention relates to a process for the purification of compound of structural formula VIII.

According to another aspect, the present invention relates to a process for purification of a compound of structural formula VIII comprising the steps of:
 a. dissolving crude compound of structural formula VIII in an ether solvent and,
 b. isolating substantially pure compound of structural formula VIII.

According to another aspect, the present invention relates to a process of preparing alcaftadine compound of structural formula I comprising the steps of:
 a. dissolving crude compound of structural formula VIII in an ether solvent,
 b. Isolating a substantially pure compound of structural formula VIII and
 c. converting a substantially pure compound of structural formula VIII into alcaftadine compound of structural formula I.

According to another aspect, the present invention relates to solvated compound of structural formula XV:

Formula XV

According to another aspect, the present invention relates to tetrahydrofuran solvated compound of structural formula XVI:

Formula XVI

According to another aspect, the present invention relates to a crystalline compound of structural formula VIII.

Another aspect of the present invention is to provide an improved process of preparing an alcaftadine compound of structural formula I.

Another aspect of the present invention is to provide an improved process of preparing alcaftadine comprising reacting a substantially pure compound of structural formula VIII with more than 20 moles of oxidizing reagent In an organic solvent to obtain an alcaftadine compound of structural formula I:

Formula VIII

Formula I

Another aspect of the present invention is to provide a substantially pure alcaftadine compound of structural formula I.

Another aspect of the present invention is to provide a process of preparing substantially pure alcaftadine compound of structural formula I comprising reacting a substantially pure compound of structural formula VIII with more than 20 moles of oxidizing reagent in an organic solvent to obtain a substantially pure alcaftadine compound of structural formula I.

Formula VIII

Formula I

BRIEF DESCRIPTION OF THE DRAWINGS

Further features and advantages of the invention will become apparent from reading the following detailed description in conjunction with the following drawings, in which like reference numbers refer to like parts.

DETAILED DESCRIPTION OF THE PREFERRED EMBODIMENT

The examples and the referenced drawings in this detailed description are merely exemplary, and should not be used to limit the scope of the claims in any claim construction or interpretation.

In an embodiment, the present invention relates to a process for the preparation of a substantially pure compound of structural formula VIII:

Formula VIII

The term "substantially pure compound of structural formula VIII" described herein refers to a compound of structural formula VIII having less than 15% of compound of structural formula XIV:

Formula XIV

In another embodiment, the present invention relates to a process for purification of compound of structural formula VIII comprising the steps of:
  a. dissolving a crude compound of structural formula VIII in an ether solvent and,
  b. isolating a substantially pure compound of structural formula VIII.

The crude compound of structural formula VIII used according to the present invention can be prepared by methods disclosed in the art such as those described in U.S. Pat. No. 5,468,743, the disclosure of which is incorporated herein by reference.

In one preferred embodiment, the purification of a compound of structural formula VIII is carried out by dissolving a crude compound of structural formula VIII in an ether solvent at a temperature in the range of 40° C. to 80° C. and maintained for 30 minutes to 2 hours. The resulting solution was cooled to 20° C. to 30° C. to obtain a pure compound of structural formula VIII.

Ether solvents can be selected from the group comprising, but not limited to, tetrahydrofuran, 1,4-dioxane, diethyl ether, diisopropyl ether, dibutyl ether, methyl tertiary butyl ether, methyl ethyl ether, methyl isobutyl ether or mixture(s) thereof.

The substantially pure compound of structural formula VIII may be isolated by any known process in the art such as filtration, centrifugation, washing, drying or the combinations thereof.

The isolated pure compound of structural formula VIII may be dried at a temperature in the range of 40° C. to 80° C. for a period of 2 hours to 12 hours under reduced pressure.

The solvates of compound of structural formula XV can be selected from the group comprising, but not limited to, tetrahydrofuran solvate, 1,4-dioxane solvate, diethyl ether solvate, diisopropyl ether solvate, dibutyl ether solvate, methyl tertiary butyl ether solvate, methyl ethyl ether solvate or methyl isobutyl ether solvate.

One example of a solvated compound of structural formula XV includes tetrahydrofuran solvated compound of structural formula XVI:

Formula XVI

•Tetrahydrofuran solvate

The isolated substantially pure compound of structural formula VIII may be crystalline or amorphous in nature.

In another embodiment, the present invention relates to a crystalline compound of structural formula VIII characterized by X-ray diffraction pattern having peaks at 8.0, 11.0, 12.8, 14.0, 15.0, 15.7, 16.9, 18.7, 19.3, 20.3, 20.6, 21.8, 22.2, 22.6, 25.2, 25.8, 27.1, 27.8, 28.8, 30.7±0.2 degrees two theta.

Figure 1:
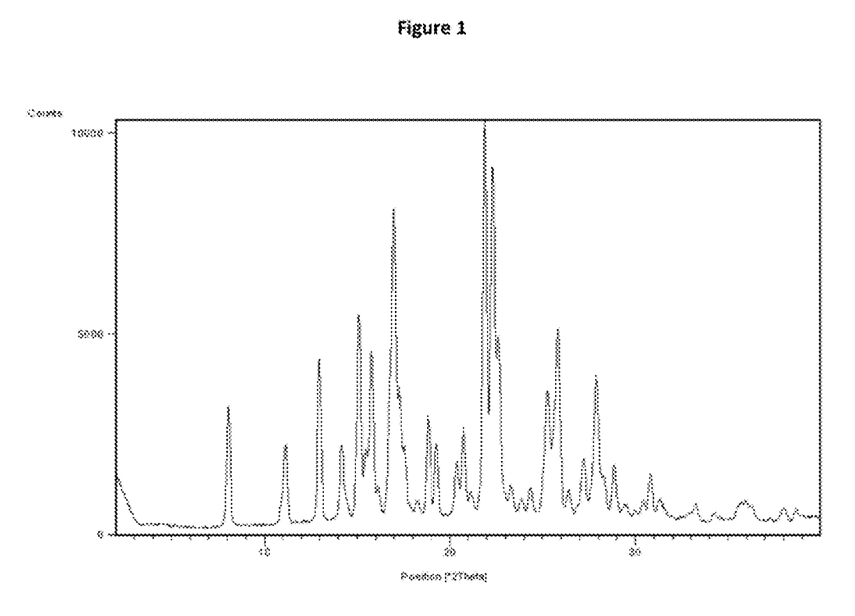
FIG. 1 depicts an X-ray diffraction pattern of a crystalline compound of structural formula VIII.

In another embodiment, the present invention relates to a crystalline compound of structural formula VIII characterized by X-ray diffraction pattern as depicted in FIG. 1.

Figure 2:
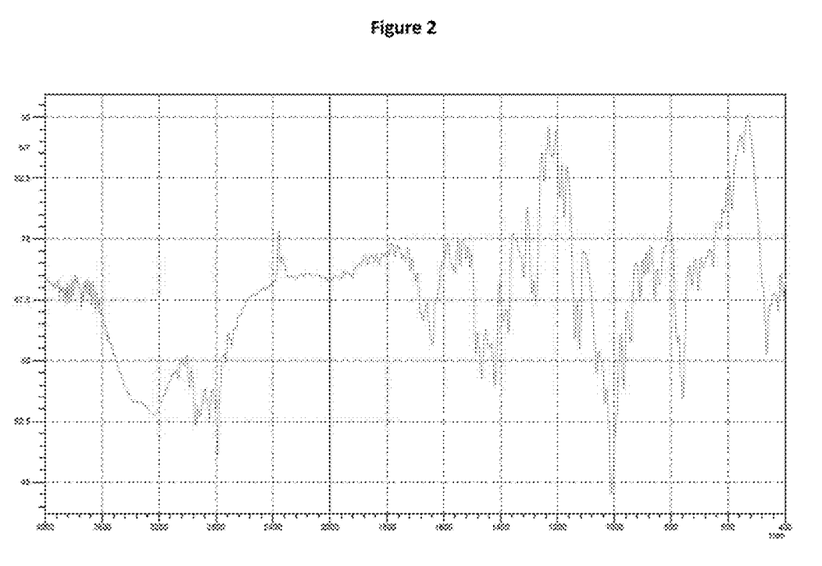
FIG. 2 depicts an infrared spectra of a crystalline compound of structural formula VIII.

In another embodiment, the present invention relates to a crystalline compound of structural formula VIII characterized by an infrared spectrum as depicted in FIG. 2.

In one example, the alcaftadine compound of structural formula I is prepared by reacting a substantially pure compound of structural formula VIII with more than 20 moles of oxidizing reagent in an organic solvent.

In another embodiment, the present invention relates to a process of preparing alcaftadine compound of structural formula I comprising the steps of:
  a. dissolving crude compound of structural formula VIII in an ether solvent,
  b. isolating a substantially pure compound of structural formula VIII and
  c. converting a substantially pure compound of structural formula VIII into alcaftadine compound of structural formula I.

In another embodiment, the present invention relates to a process of preparing substantially pure alcaftadine compound of structural formula I comprising reacting a substantially pure compound of structural formula VIII with more than 20 moles of oxidizing reagent in an organic solvent to obtain a substantially pure alcaftadine compound of structural formula I.

The reaction of a substantially pure compound of structural formula VIII with more than 20 moles of oxidizing reagent in an organic solvent can be carried out at a temperature in the range of 40° C. to 80° C. for a period of 2 hours to 24 hours.

The oxidizing reagent may be added in one lot or in several lots.

An oxidizing reagent can be selected from the group comprising, but not limited to, manganese dioxide, silver nitrate, selenium dioxide or ceric ammonium nitrate or the like or mixtures thereof.

An organic solvent according to present invention can be selected from the group comprising, but not limited to, ketones, alcohols, esters, nitriles, halogenated aliphatic hydrocarbon solvents, ethers or mixtures thereof.

The ketone solvents can be selected from the group comprising, but not limited to, acetone, methyl ethyl ketone, methyl isobutyl ketone, dibutyl ketone, diethyl ketone, dipropyl ketone, diisopropyl ketone, methyl butyl ketone, methyl propyl ketone, methyl isopropyl ketone, ethyl isopropyl ketone or mixture(s) thereof.

The alcohol solvents can be selected from the group comprising, but not limited to, methanol, ethanol, propanol, isopropanol, butanol, isobutanol, t-butanol, pentanol or mixture(s) thereof.

The ester solvents can be selected from the group comprising, but not limited to, ethyl acetate, propyl acetate, isopropyl acetate, butyl acetate, tertiary butyl acetate, pentyl acetate or mixture(s) thereof.

The nitrile solvents can be selected from the group comprising, but not limited to, acetonitrile, propionitrile or mixture(s) thereof.

The halogenated aliphatic hydrocarbon solvents can be selected from the group comprising, but not limited to, dichloromethane, dichloroethane, chloroform, carbon tetrachloride or mixture(s) thereof.

The ether solvents can be selected from the group comprising, but not limited to, tetrahydrofuran, dioxane, diethyl ether, diisopropyl ether, dibutyl ether, methyl tertiary butyl ether, methyl ethyl ether, methyl isobutyl ether or mixture(s) thereof.

The alcaftadine compound of structural formula I can be isolated by cooling the reaction mixture at a temperature in the range of 25-35° C. followed by filtering the reaction mixture in order to obtain a filtrate. The filtrate obtained may be washed with organic solvent and then organic layer can be separated, washed with water and dried over sodium sulphate.

The resulting organic layer containing alcaftadine compound of structural formula I may be concentrated under reduced pressure to obtain a residue of alcaftadine compound of structural formula I. The residue of alcaftadine compound of structural formula I may be crystallized by an ether solvent to obtain a substantially pure alcaftadine compound of structural formula I.

The isolated substantially pure alcaftadine compound structural formula I may be dried at a temperature in the range of 40-60° C. for a period of 2 hours to 10 hours under reduced pressure.

The term "substantially pure alcaftadine compound of structural formula I" described herein refers to an alcaftadine compound of structural formula I having less than 5% of a compound of structural formula VIII:

Formula VIII

EXAMPLES

In the following examples, the preferred embodiments of the present invention are described only by way of illustrating the process of the invention. However, these are not intended to limit the scope of the present invention in any way.

Example 1

Purification of a Compound of Structural Formula VIII

A crude compound of structural formula VIII (50 grams) was dissolved in tetrahydrofuran (500 ml) at 60-65° C. and maintained for 1 hour. The resulting solution was cooled to 25-35° C. to obtain solids. The resulting solids were filtered, washed with tetrahydrofuran (50 ml) and dried at 45-55° C. under reduced pressure for 8 hours to obtain a pure compound of structural formula VIII.

Yield: 35 grams
Purity: 99.9% (By HPLC)

Example 2

Purification of a Compound of Structural Formula VIII

A crude compound of structural formula VIII (10 grams) was dissolved in tetrahydrofuran (100 ml) at 60-65° C. and maintained for 1 hour. The resulting solution was cooled to 25-35° C. to obtain solids. The resulting solids were filtered, washed with tetrahydrofuran (10 ml) and dried at 45-55° C. under reduced pressure for 5 hours to obtain a pure compound of structural formula VIII.

Yield: 8.5 grams
Purity: 99.9% (By HPLC)

Example 3

Purification of a Compound of Structural Formula VIII

A crude compound of structural formula VIII (10 grams) was dissolved in 1,4-dioxane (100 ml) at 60-65° C. and maintained for 1 hour. The resulting solution was cooled to 25-35° C. to obtain solid. The resulting solids were filtered, washed with 1,4-dioxane (20 ml) and dried at 45-55° C.

under reduced pressure for 6 hours to obtain a pure compound of structural formula VIII.

Yield: 8.7 grams
Purity: 99.8% (By HPLC)

Example 4

Preparation of a Substantially Pure Alcaftadine Compound of Structural Formula I To a solution of a substantially pure compound of structural formula VIII (40 grams) in chloroform (4000 ml), a first lot of manganese dioxide (200 grams) was added at 25-35° C. and then the resulting reaction mixture was heated to 60-65° C. and stirred for 4 hours. The second lot of manganese dioxide (200 grams) was then added to the reaction mixture at 60-65° C. and stirred for 4 hours. In this manner third, fourth, fifth and sixth lots of manganese dioxide (200 grams) were added to the reaction mixture at 60-65° C. and after each lot addition, the reaction mixture was stirred for 4 hours. The resulting reaction mixture was cooled to 25-35° C., filtered and washed with chloroform (1000 ml). The resulting organic layer was washed with water (2×400 ml), dried over sodium sulphate (200 grams) and concentrated under reduced pressure to obtain a residue. Diethyl ether (150 ml) was added to the resulting residue and then was stirred for 2 hours at 25-35° C. to obtain a suspension. The resulting suspension was filtered, washed with diethyl ether (50 ml) and dried under reduced pressure at 45-55° C. for 8 hours to obtain a substantially pure alcaftadine compound of structural formula I.

Yield: 30 grams
Purity: 98.7% (By HPLC)

Example 5

Preparation of a Substantially Pure Alcaftadine Compound of Structural Formula I To a solution of a substantially pure compound of structural formula VIII (20 grams) in chloroform (2000 ml), manganese dioxide (600 grams) was added at 25-35° C. and then the resulting reaction mixture was heated to 60-65° C. and stirred for 18 hours. The resulting reaction mixture was cooled to 25-35° C., filtered and washed with chloroform (500 ml). The resulting organic layer was washed with water (2×200 ml), dried over sodium sulphate (100 grams) and concentrated under reduced pressure to obtain a residue. Diethyl ether (100 ml) was added to the resulting residue and stirred for 1 hour at 25-35° C. to obtain a suspension. The resulting suspension was filtered, washed with diethyl ether (25 ml) and dried under reduced pressure at 45-55° C. for 6 hours to obtain a substantially pure alcaftadine compound of structural formula I.

Yield: 15 grams
Purity: 98.8% (By HPLC)

Example 6

Preparation of a Substantially Pure Alcaftadine Compound of Structural Formula I

To the solution of substantially pure compound of structural formula VIII (40 grams) in chloroform (4000 ml), manganese dioxide (1200 grams) was added at 25-35° C. and then the resulting reaction mixture was heated to 60-65° C. and stirred for 16 hours. The resulting reaction mixture was cooled to 25-35° C., filtered and washed with chloroform (1000 ml). The resulting organic layer was washed with water (2×400 ml), dried over sodium sulphate (200 grams) and concentrated under reduced pressure to obtain a residue. Diethyl ether (200 ml) was added to the resulting residue and then stirred for 1 hour at 25-35° C. to obtain a suspension. The resulting suspension was filtered, washed with diethyl ether (50 ml) and dried under reduced pressure at 45-55° C. for 8 hours to obtain a substantially pure alcaftadine compound of structural formula I.

Yield: 30 grams
Purity: 98.9% (By HPLC)

The scope of the claims should not be limited by the preferred embodiments and examples described herein, but should be given the broadest interpretation consistent with the written description as a whole.

What is claimed is:

1. An improved process of preparing a substantially pure alcaftadine compound of structural formula I comprising the following reaction scheme:

Formula VIII

Formula I wherein the process includes:
a step of reacting a substantially pure compound of structural formula VIII with the oxidizing reagent at a mole ratio of the oxidizing reagent to the substantially pure compound of structural formula VIII being 26:1 or at a mole ratio greater than said mole ratio of 26:1 in an organic solvent to obtain the substantially pure alcaftadine compound of structural formula I, and the substantially pure compound of structural formula VIII is a compound of structural formula VIII having less than 15% of a compound of structural formula XIV:

Formula XIV

2. The process according to claim 1, wherein the reaction is carried out at a temperature in the range of 40° C. to 80° C. for a period of 2 hours to 24 hours.

3. The process according to claim 1, wherein the oxidizing reagent is selected from the group consisting of manganese dioxide, silver nitrate, selenium dioxide, eerie ammonium nitrate and mixtures thereof.

4. The process according to claim 1, wherein the oxidizing reagent added in one lot or in several lots.

5. The process according to claim 1, wherein the organic solvent is selected from the group consisting of ketone solvents including acetone, methyl ethyl ketone, methyl isobutyl ketone, dibutyl ketone, diethyl ketone, dipropyl ketone, diisopropyl ketone, methyl butyl ketone, methyl propyl ketone, methyl isopropyl ketone, ethyl isopropyl ketone and mixture(s) thereof; alcohol solvents including methanol, ethanol, propanol, isopropanol, butanol, isobutanol, t-butanol, pentanol and mixture(s) thereof; ester solvents including ethyl acetate, propyl acetate, isopropyl acetate, butyl acetate, tertiary butyl acetate, pentyl acetate and mixture(s) thereof; nitrile solvents including acetonitrile, propionitrile and mixture(s) thereof; halogenated aliphatic hydrocarbon solvents including dichioromethane, dichloroethane, chloroform, carbon tetrachloride and mixture(s) thereof; and or in combination with ether solvents including tetrahydrofuran, dioxane, diethyl ether, diisopropyl ether, dibutyl ether, methyl tertiary butyl ether, methyl ethyl ether, methyl isobutyl ether and mixture(s) thereof.

6. An improved process of preparing a substantially pure alcaftadine compound of structural formula I comprising the steps of:
    reacting a substantially pure compound of structural formula VIII with an oxidizing reagent at a mole ratio of the oxidizing reagent to the substantially pure compound of structural formula VIII being 26:1 or at a mole ratio greater than said mole ratio of 26:1 in an organic solvent; the substantially pure compound of structural formula VIII being a compound of structural formula VIII having less than 15% of a compound of structural formula XIV:

Formula XIV cooling the reaction mixture at a temperature in the range of about 25-35° C.;
filtering the reaction mixture to obtain a filtrate;
washing the filtrate with an organic solvent and then with water;
drying to obtain a residue of an alcaftadine compound; and
crystallizing the residue using an ether solvent to obtain a substantially pure alcaftadine compound of structural formula I, wherein the substantially pure alcaftadine compound is an alcaftadine compound of structural formula I having less than 5% of a compound of structural formula VIII, the compound of structural formula VIII having the formula:

Formula VIII

7. The process according to claim 6, wherein the substantially pure alcaftadine compound of structural formula I is dried at a temperature in the range of 40-60° C. for a period of 2 hours to 10 hours under reduced pressure.

8. A substantially pure alcaftadine compound of structural formula I prepared by the process according to claim 6 and having the formula:

Formula I wherein the substantially pure alcaftadine compound of structural formula I has less than 5% of a compound of structural formula VIII, the compound of structural formula VIII having the formula:

Formula VIII

* * * * *